United States Patent [19]

Wade

[11] 4,173,521
[45] Nov. 6, 1979

[54] PHOTOSENSITIVE REDOX SOLUTIONS

[75] Inventor: Robert C. Wade, Ipswich, Mass.

[73] Assignee: Thiokol Corporation, Newtown, Pa.

[21] Appl. No.: 196,804

[22] Filed: Nov. 8, 1971

Related U.S. Application Data

[63] Continuation-in-part of Ser. No. 842,716, Jul. 17, 1969, abandoned.

[51] Int. Cl.$^2$ ............................ B01J 1/10; B01J 31/12
[52] U.S. Cl. ......................... 204/157.1 R; 204/158 R; 252/429 A; 252/429 B
[58] Field of Search .................... 204/157.1 R, 158 R; 252/429 R, 429 B

[56] References Cited

U.S. PATENT DOCUMENTS

| | | | |
|---|---|---|---|
| 2,984,658 | 5/1961 | Seydel et al. | 260/94.9 |
| 3,073,766 | 1/1963 | Brown et al. | 204/154 |
| 3,114,718 | 12/1963 | Elston | 252/429 |
| 3,284,329 | 11/1966 | Aftandilian | 204/157.1 |

Primary Examiner—F. C. Edmundson
Attorney, Agent, or Firm—Stanley A. Marcus; J. Harold Boss

[57] ABSTRACT

The invention provides aqueous solutions of (1) the reaction product of anhydrous trimethyl borate with titanium tetrachloride and (2) polyvinyl alcohol, preferably not exceeding about 0.5 weight percent of each. These solutions have a pH of about 1 but when ammonium hydroxide is added the pH may be raised to about 10 without precipitation of titanium or gelation of the polyvinyl alcohol.

When the pH of the above solutions is adjusted to between about 2 and about 10, the solutions are photosensitive. When these solutions are in a confined zone, sunlight or actinic radiation in the range between ultraviolet light and the lower wavelengths of the visible spectrum causes oxygen from the air above the solutions to be consumed until it is all gone. Then, reduction of the colorless dissolved Ti(IV) compound to the dark blue Ti(III) state occurs without precipitation of the Ti(III) product or reoxidation to Ti(IV). The blue Ti(III) solution is quickly reoxidized by reexposure to air. Similar photosensitive solutions are formed with polyvinyl alcohol and other Ti(IV) compounds, such as (1) the tetravalent titanium compound conforming substantially to the formula $Cl_2Ti(OR)_2$ where R is H, $CH_3$, $C_2H_5$, $C_3H_7$ or $C_4H_9$; (2) titanyl sulfate, and (3) titanyl chloride. The polyvinyl alcohol may be replaced by other complexing agents, such as N-hydroxyethylenediaminetriacetic acid, diethanolglycine, glucoheptanoic acid, arabonic acid, glusonic acid, galactonic acid, saccharic acid, mucic acid, and the sodium and ammonium salts of these compounds.

6 Claims, No Drawings

PHOTOSENSITIVE REDOX SOLUTIONS

This application is a continuation-in-part of my application Ser. No. 842,716, filed July 17, 1969, now abandoned.

The invention relates to photosensitive redox solutions and to methods for reducing compounds or bleaching substances normally reducible or bleachable with Ti(III) compounds.

My copending application Ser. No. 630,845 filed Apr. 14, 1967, now abandoned, describes products of unknown complex chemical structure which are the reaction products of anhydrous trimethyl borate with anhydrous titanium tetrachloride. These complex products are prepared by reacting anhydrous trimethyl borate with anhydrous titanium tetrachloride in an inert anhydrous solvent, such as methylene chloride, chloroform, carbon tetrachloride, or an excess of trimethyl borate. When the evolution of methyl chloride ceases, the reaction is essentially complete. By evaporating the solvent or excess trimethyl borate from the reaction mixture, the solid product is obtained. Elemental analysis indicates that from 1 to 2 moles of trimethyl borate will react with one mole of titanium tetrachloride.

My copending application Ser. No. 816,065, filed Apr. 14, 1969, now abandoned, describes aqueous solutions of polyvinyl alcohol and the reaction product of anhydrous trimethyl borate with anhydrous titanium tetrachloride which may be used to coat various substrates, such as cotton, glass, leather, paper and starch and which when dried forms a substantially water insoluble adherent coating on the substrate.

In forming the aqueous solutions of these complex reaction products and polyvinyl alcohol, equal weight percent of each is preferred although an excess of polyvinyl alcohol may be used. There is no benefit in the use of more than about 1 weight percent of either the complex reaction product of polyvinyl alcohol. When not more than about 0.5 weight percent of each is used, a solution having a pH of about 1 is formed, but the solutions may be neutralized, that is, raised to a pH of 7 or as high as about 10 by the addition of ammonium hydroxide without precipitation of titanium or gelation of the polyvinyl alcohol.

I have now discovered that when the pH of the above aqueous solutions of polyvinyl alcohol and the complex reaction of titanium tetrachloride and trimethyl borate is raised from its normal pH of about 1, to a value between about 2 to about 10 and preferably 4 to 9 by the addition of ammonium hydroxide, the solutions are photosensitive. When these solutions are in a confined zone, sunlight or actinic radiation in the range between ultraviolet light and the lower wavelengths of the visible spectrum causes oxygen from the air above the solution to be consumed until it is all gone. Then, reduction of the colorless dissolved Ti(IV) compound to the dark blue Ti(III) state occurs without precipitation or reoxidation to Ti(IV) of the Ti(III) product. The blue Ti(III) solution is quickly reoxidized by re-exposure to air. Similar photosensitive solutions are formed with other Ti(IV) compounds such as (1) the tetravalent titanium compound conforming substantially to the formula $Cl_2Ti(OR)_2$ where R is H, $CH_3$, $C_2H_5$, $C_3H_7$ or $C_4H_9$; (2) $(TiOSO_4)$ titanyl sulphate, and (3) $(TiOCl_2)$ titanyl chloride. The polyvinyl alcohol may be replaced by other complexing agents, such as the chelating agents N-hydroxyethylenediaminetriacetic acid, diethanolglycine, glucoheptanoic acid, arabonic acid, gluconic acid, galactonic acid, saccharic acid, mucic acid, and the sodium or ammonium salts of these compounds.

Thus, the invention provides a novel method for reducing compounds normally reducible with Ti(III) reducing agents. The method comprises contacting the compound to be reduced in a confined reaction zone free of oxygen with one of the above photosensitive redox solutions and then subjecting the photosensitive solution to active radiation in the range between the lower wavelengths of the visible spectrum and ultraviolet light.

For the Ti(IV) compound $TiOSO_4$, the commercially available titanyl sulfate solution may be used as illustrated in the following Example 5.

The $Cl_2Ti(OR)_2$ compound can be prepared, for example, by the addition of $TiCl_4$ to cold water to give an aqueous milky colloidal suspension of the desired concentration. This solution can be added to the polyvinyl alcohol or chelating agent solution and neutralized to the desired pH with ammonia with no need to isolate the initial reaction product of $TiCl_4$ and water.

Where $TiCl_4$ is reacted with a lower aliphatic alcohol, the $TiCl_4$ is generally added in excess of alcohol. Hydrochloric acid is formed which may be removed along with excess alcohol by vacuum evaporation at temperatures up to 100° C. The resulting solid product corresponds closely to the formula $Cl_2Ti(OR)_2$ where OR corresponds to the starting alcohol ROH. These solid products may then be dissolved in water to give clear colorless solutions of the desired concentration. These solutions may then be added to water solutions containing sufficient polyvinyl alcohol or chelating agent so that the pH may be adjusted to between 2 and 10 with ammonium hydroxide or an acid without precipitation of titanium or gelation of the polyvinyl alcohol. These solutions are now photosensitive.

The amount of complexing agent required to prevent precipitation of the Ti(IV) ion varies with the nature of the complexing agent, the starting Ti(IV) compound, and the final pH desired. In general, at least one part by weight of the complexing agent is required for each part of the starting Ti(IV) compound.

So far as I am aware, the photochemical reduction of aqueous solutions containing Ti(IV) to Ti(III) was not previously known. Normally, this reduction is carried out in strongly acid solutions by reduction with a metal, such as zinc, or by electrolysis. It is surprising that the photochemical reductions leading to Ti(III) solutions do not take place in solutions of the Ti(IV) compounds and polyvinyl alcohol or other complexing agent if the pH is not in the range of about 2 to 10. At a pH of less than about 2, most of these solutions turn an intense yellow color in sunlight.

As illustrative of compounds which may be reduced by these aqueous photosensitive redox systems I may mention organic compounds, such as quinones and vat dyes, and inorganic compounds, such as aqueous solutions of salts of mercury and silver. These photosensitive redox solutions are also capable of bleaching cotton, groundwood, unbleached kraft pulp and wool. These reducing systems appear to be catalytic in that less than the stoichiometric amount of Ti(III) ion need be present to carry out the reduction. The actinic radiations continually reduce Ti(IV) to Ti(III) as the Ti(III) is chemically oxidized by the substrate back to Ti(IV).

These solutions also may be used for coating anionic substrates such as cotton, glass, leather, wool, and paper to form a water-insoluble coating thereon when dried.

The invention is illustrated further by the following examples.

EXAMPLE 1

A 500 ml, four neck flask was fitted with a water cooled reflux condenser, an ice condenser and a dry ice condenser all connected in series. A thermometer and dropping funnel and stirrer were also fitted into the flask.

The flask was purged with dry nitrogen and charged with 200 g of redistilled methylene chloride and 104 g (2 moles) of redistilled methyl borate. One gram mole of titanium tetrachloride was added dropwise over a period of about two hours, heat evolved, and yellow solids quickly formed. When about half of the $TiCl_4$ had been added, methyl chloride started to come off and was condensed out in the dry ice trap. When all of the $TiCl_4$ had been added, heat was applied to the flask to keep the methylene chloride refluxing. As methyl chloride was evolved, the yellow solids slowly disappeared. Refluxing was continued for about 3.5 hours until no more $CH_3Cl$ came off and a homogeneous yellow solution was obtained. The maximum temperature reached during this experiment was about 56° C.

The homogeneous yellow solutions was quite fluid at room temperature. However, as methylene chloride was vacuum evaporated, the solution became increasingly more viscous, reaching a taffy-like consistency and finally a glassy-like consistency. Final removal of methylene chloride was accomplished by heating to 65° C. under a vacuum of 10 mm of mercury for 24 hours. The yield of light yellow solid product was 141 g, which analyzed as follows:

Ratios: Ti/B=1/1.9, Ti/Cl=1/2 B/OCH—3=1/1.8

EXAMPLE 2

47.5 grams of $TiCl_4$ was added with good stirring to 100 ml of anhydrous methanol. Heat was evolved along with some HCl. A clear yellow solution resulted. Excess methanol was removed by vacuum evaporation to give a very light yellow solid product which analyzed closely to $Cl_2Ti(OCH_3)_2$. 10 grams of this solid product was dissolved in 1000 ml of water to give a clear colorless solution of pH=1.5. This solution was used to prepare complexes with polyvinyl alcohol and chelating agent solutions as described in later examples.

Similar clear solutions were prepared from the reaction products of $TiCl_4$ with ethanol and isopropanol.

EXAMPLE 3

10 grams of $TiCl_4$ was slowly added with good stirring to 1000 ml of ice water. The $TiCl_4$ reacted to give a slightly opaque milky colloidal suspension containing 1% $TiCl_4$ of pH=1.2. The suspension did not settle on standing but was truly colloidal. This product is believed to be polymeric hydrated $TiCl_4$ or $(Cl_2Ti(OH)_2)_n$. This solution was used to prepare complexes with polyvinyl alcohol solutions and chelating agents as described in the following examples.

EXAMPLE 4

2 liters of an aqueous solution containing ½% of the complex solid product of Example 1 and ½% of "Evanol 72-60" (T.M. E.I. du Pont) polyvinyl alcohol was prepared by adding a 1% aqueous solution of the complex to a product to 1% polyvinyl alcohol solution. The pH of this solution was about 1.7. This solution was divided into 10–200 ml aliquots. The first aliquot was bottled without pH adjustment. The remaining aliquots were adjusted by addition of dilute $NH_4OH$ to the following pH values 2,3,4,5,6,7,8,9, and 10 to give clear colorless solutions. These were also placed in a 1-pint clear glass bottles fitted with serum caps. The air in the bottles was displaced by nitrogen. The bottles were exposed to an ultraviolet "black light" whose primary emission lies at about 3650 angstroms. All of the bottles from pH 2-10 quickly developed a blue color characteristic of Ti(III) solutions. The most intense colors developed in those bottles whose pH was 4–9. A very faint blue color was present in the bottle which had no pH adjustment (pH=1.7). bottles were exposed to sunlight for 8 hours. The color became more intense in all bottles whose pH was 4–9, and slightly more intense in those whose pH was 2,3, and 10. No color change occurred in the solution, pH 1.7.

The same results were obtained using equal volumes of the Ti(IV) solutions described in Examples 2 and 3 together with solutions containing 0.5–1% polyvinyl alcohol or 1–2% diethanol glycine, or 1–2% N-hydroxyethylenediaminetriacetic acid, 1–3% glucoheptanoic acid, or the sodium salts of these chelating agents.

EXAMPLE 5

A sample of commercially available titanyl sulfate solution containing 13.6% $TiO_2$ and excess $H_2SO_4$ was diluted with water so that it now contained 1% $TiO_2$. One volume of this solution was mixed with 3 volumes of 1% polyvinyl alcohol solution. The pH of this mixture was 1.0. Then $NH_4OH$ was added with stirring. As the pH was raised to 6.5, part of the Ti(IV) ion precipitated as a white flocey solid. Not all of the Ti(IV) was precipitated, however. 200 ml of this mixture was placed in a one-half pint clear glass bottle fitted with a serum cap. The air in the free space was purged with nitrogen. The bottle and contents were exposed to sunlight for a few hours. The colorless colloidal suspension slowly turned the deep blue color of Ti(III), indicating that a photoreduction had occurred. When the bottle was opened and aerated, the deep blue color disappeared and Ti(III) was reoxidized to Ti(IV).

EXAMPLE 6

Another bottle was prepared with a solution containing ½% of the complex product of Example 1 and ½% polyvinyl alcohol. The pH was adjusted to 6 with $NH_4OH$. This was placed in a bottle and capped. Air was not displaced. This bottle was exposed to sunlight daily for two weeks. No color change was noted. Then a blue color began to develop during the daylight hours when in sunlight, but which slowly faded in the dark. Three days of further exposure to sunlight caused the color to intensify each day and after the third day no longer faded in the dark. The color became an intense blue with no precipitation noted. The serum cap of the bottle was punctured with a needle connected to a gas buret. The vacuum in the bottle as measured by the gas buret indicated all of the oxygen had been consumed in the free space. Air was admitted and the bottle recapped and shaken. The blue color disappeared instantly indicating reoxidation of the blue Ti(III) to the colorless Ti(IV). This bottle was re-exposed to sunlight for another two weeks when the same blue color again developed. The reduction-oxidation cycle described in this example was repeated four times. The polyvinyl alcohol was examined and found to have been oxidized.

In a similar experiment a 1 pt. bottle containing 200 ml of this same pH 6 solution and whose free space contained air was connected to a manometer. During three weeks exposure to sunlight the volume of gas in the system continually decreased indicating oxygen was being consumed. When about all of the oxygen in the system had been consumed as indicated by the gas volume decrease, the blue color of Ti(III) developed and remained without fading.

EXAMPLE 7

A 1 pint bottle containing 200 ml of ½% of the Ti complex of Example 1 and ½% polyvinyl alcohol solution (pH=1.7) and whose free space contained air, was exposed to sunlight for three weeks. Initially, a very faint blue color was noted. This quickly changed and the solution developed an intense deep yellow color. At no time did the intense blue Ti(III) color develop.

EXAMPLE 8

200 ml of a Ti(IV)-polyvinyl alcohol solution (pH 7) as prepared in Example 4 was placed in clear glass bottles. To this was added one ml of a concentrated vat dye known as Vat Yellow-2. (Color Index No. 67300/1). The bottle was capped with a serum cap and the air removed and replaced with nitrogen. The bottle was placed in the sunlight. Over the course of about 1 hour, the dye was reduced from the original bright yellow color to an orange color. This is the characteristic color of the leuco-acid form of the dye. In a similar experiment a vat dye, Vat Green B (Color Index No. 69825) was reduced from the original blue green color to the purple leuco acid from in a few hours exposure to sunlight. Likewise the vat dye, Red FBB, (Color Index No. 67000) was reduced form a bright pink color to the leuco acid color which is a reddish brown after about three hours exposure to sunlight.

It is clear that these photosensitive redox systems are capable of reducing vat dyes when catalyzed by light in the lower range of the visible spectrum.

EXAMPLE 9

200 ml of a Ti(IV)-polyvinyl alcohol solution (pH 6) as prepared in Example 4 was placed in a clear glass bottle together with 0.1 g of the sodium salt of 2-anthraquinone sulfonic acid. The bottle was capped with a serum cap and the air displaced with nitrogen. The bottle was placed in sunlight. Within a few minutes a red color developed in the solution which is characteristic of the leuco or reduced form of this compound. (The original oxidized solution was colorless). This demonstrates that quinones are rapidly reduced by this system when catalyzed by the lower wavelengths of visible light.

EXAMPLE 10

10 ml of a dark blue Ti(III) solution (pH=4) prepared by photo reduction as described in Example 4 was injected into 25 ml and an aqueous solution of 0.1M mercuric nitrate contained in a bottle under nitrogen atmosphere. Within a few moments mercury metal started to precipitate. More mercury precipitated when this solution was exposed to sunlight.

The same experiment was repeated where silver nitrate was substituted for mercuric nitrate. In this case, a brown colloidal silver precipitate formed. The color and amount of precipitate intensified when the bottle was exposed to sunlight for about 30 minutes.

It is apparent that catalytic amounts of the Ti(III) complex polyvinyl alcohol solution can be used to reduce water soluble metal salts such as silver and mercury nitrate when these mixtures are exposed to the lower wavelengths of visible light.

EXAMPLE 11

Four 1 pint glass bottles each containing 200 ml of the ½% polyvinyl alcohol titanium tetrachloride-methyl borate reaction product (solution pH=6) as prepared in Example 4 were set up. In the first bottle was placed a sample of unbleached cotton fabric. In the second was placed a piece of unbleached wool fabric. In the third was placed a piece of 100% groundwood board. In the fourth was placed a piece of unbleached kraft paper. The bottles were capped with serum caps and the air space replaced with nitrogen. The bottles were exposed to bright sunlight for about 8 hours. A deep blue color developed in each bottle. Then the solution was poured off of the substrate, the substrate washed three times with distilled water, blotted and air dried at room temperature. The brightness was again measured. All samples were bleached by this process as shown in the following table:

| Sample No. | Substrate | Brightness Unbleached | (Photovolt) Bleached | B |
|---|---|---|---|---|
|  | cotton | 79 | 82.3 | 3.3 |
| 2 | wool | 48 | 53.1 | 5.1 |
| 3 | groundwood | 60.5 | 63.0 | 2.5 |
| 4 | kraft paper | 25.1 | 26.5 | 1.4 |

EXAMPLE 12

50 ml of a 1% aqueous solution of the product produced in Example 1 was dissolved in water. This was added carefully to 50 ml of a 1% aqueous solution of polyvinyl alcohol (Elvanol 72-60). The resulting solution containing 0.5% of the titanium compound and 0.5% of the polyvinyl alcohol had a pH of about 1. Dilute ammonium hydroxide was added carefully with good stirring until the pH was 7. No precipitation of the titanium occurred, nor did the polyvinyl alcohol gel. A portion of this solution was treated with additional ammonium hydroxide to a pH of 10. No precipitation or gelation occurred.

Cotton fabric was coated with these solutions and dried at 130° C. The polyvinyl alcohol coating imparted a permanent stiffening to the fabric which survived 15 standard home launderings. A similar experiment was performed where the cotton was coated only with the 0.5% polyvinyl alcohol solution. Almost all of this coating was removed after 3 washings.

EXAMPLE 13

A 5% solution of polyvinyl alcohol was prepared. To this solution was added an equal volume of 0.2% solution of the compound produced in Example 1. No precipitation or gelation occurred. The resulting solution contained 0.1 percent of the complex titanium compound of Example 1 and 2.5 percent of polyvinyl alcohol. pH of this solution was about 3. Ammonium hydroxide was added until the pH reached 7. No precipitation of titanium oxide occurred, but gelation of the polyvinyl alcohol did occur starting at a pH of between 4 and 5.

I claim:

1. The method for reducing a compound normally reducible with Ti (III) which comprises contacting the compound to be reduced in a confined reaction zone free of oxygen with an aqueous solution having a pH between about 2 and about 10 and containing (1) from about 0.1 to 3 weight percent of a titanium (IV) compound and (2) from about 0.5 to 3 weight percent of a complexing agent, the weight percent of said complexing agent being at least equal to that of said titanium (IV) compound, said titanium (IV) compound being selected from the group consisting of (a) the reaction product of substantially anhydrous trimethyl borate with substantially anhydrous titanium tetrachloride, (b) a water soluble titanium compound conforming substantially to the formula $CL_2Ti(OR)_2$ where R is selected from the group consisting of H, $CH_3$, $C_3H_7$ and $C_4H_9$, (c) titanyl sulfate solutions and (d) titanyl chloride solutions, said complexing agent being selected from the group consisting of N-hydroxy - ethylene - diaminetri - acetic acid, diethanol glycine, glucoheptanoic acid, succharic acid, mucid acid, the sodium and ammonium salts of these acids, polyvinyl alcohol and mixtures thereof, and subjecting said solution to actinic radiation between the lower wavelengths of the visible spectrum and ultraviolet light.

2. The method as claimed by claim 1 wherein the titanium (IV) compound is the reaction product of trimethyl borate and titanium tetrachloride.

3. The method as claimed by claim 1 wherein the titanium (IV) compound is a compound conforming substantially to the formula $Cl_2Ti(OR)_2$ where R is selected from the group consisting of H, $CH_3$, $C_2H_5$, $C_3H_7$ and $C_4H_9$.

4. The method as claimed by claim 1 wherein the titanium (IV) compound is titanyl sulfate solution.

5. The method as claimed by claim 1 wherein the titanium (IV) compound is titanium chloride solution.

6. The method as claimed by claim 2 wherein the complexing agent is polyvinyl alcohol.

* * * * *